(12) United States Patent
Ford et al.

(10) Patent No.: US 7,781,611 B2
(45) Date of Patent: Aug. 24, 2010

(54) NITRO-SULFOBENZAMIDES

(75) Inventors: Mark James Ford, Bad Soden (DE); Jan Vermehren, Idstein (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/732,006

(22) Filed: Dec. 7, 2000

(65) Prior Publication Data

US 2001/0020092 A1 Sep. 6, 2001

(30) Foreign Application Priority Data

Dec. 9, 1999 (DE) .................. 199 59 291

(51) Int. Cl.
*C07C 309/27* (2006.01)
*C07C 309/29* (2006.01)
(52) U.S. Cl. .................. 562/47; 562/65; 562/72; 562/73
(58) Field of Classification Search .................. 562/47, 562/65, 72, 73
See application file for complete search history.

(56) References Cited

U.S. PATENT DOCUMENTS

| 3,055,928 A | 9/1962 | Flores et al. ............ 260/456 |
| 5,550,237 A | 8/1996 | Vermehren ............ 560/13 |

FOREIGN PATENT DOCUMENTS

| CA | 2224612 | 6/1996 |
| DE | 43 34 949 | 5/1994 |
| WO | WO 97/16419 | 5/1997 |

OTHER PUBLICATIONS

C. A. Grob et al, Helvetica Chimica Acta, vol. 32, 1949, pp. 172-184, also referred to as XP 000973908.

*Primary Examiner*—Venkataraman Balasubramanian
(74) *Attorney, Agent, or Firm*—Frommer Lawrence & Haug LLP

(57) ABSTRACT

The present invention relates to a compound of the formula (I)

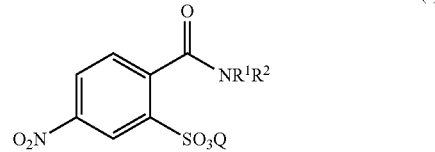

(I)

wherein
$R^1$ is an unsubstituted or substituted hydrocarbon radical having a total of 1 to 10 carbon atoms, preferably 1 to 6 carbon atoms,
$R^2$ is an unsubstituted or substituted hydrocarbon radical having a total of 1 to 10 carbon atoms, preferably 1 to 6 carbon atoms, or the group
$NR^1R^2$ is a heterocyclic ring having 3 to 8 ring atoms which is unsubstituted or substituted and contains the nitrogen atom of the group $NR^1R^2$ as ring heteroatom and may also contain one or two further ring heteroatoms from the group consisting of N, O and S, and
Q is H or a cation.
The compounds of the present invention can advantageously be used for the preparation of sulfonylureas and their precursors such as sulfochlorides or sulfonamides.

14 Claims, No Drawings

NITRO-SULFOBENZAMIDES

The invention relates to new substituted benzamides and the technical field of chemical processing for preparing substituted benzamides which can be employed for preparing herbicidally active sulfonylurea compounds, intermediates or products intended for use in crop protection.

U.S. Pat. Nos. 3,055,928 and 5,550,237 disclose various substituted sulfobenzamides. However, these compounds cannot be readily used for the synthesis of sulfonylurea herbicides and their precursors.

Accordingly an object of the present invention is to provide new sulfobenzamides that can advantageously be used for the preparation of herbicidally active sulfonylureas and their prescursors such as sulfochlorides or sulfonamides. Another object of the present invention is to provide an improved process for the preparation of herbicidally active sulfonylureas and their prescursors such as sulfochlorides or sulfonamides.

The present invention thus relates to new 4-nitro-2-sulfobenzamides of the formula (I),

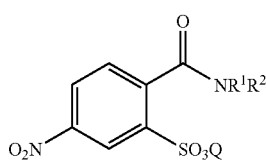

wherein
$R^1$ is an unsubstituted or substituted hydrocarbon or radical having a total of 1 to 10 carbon atoms, preferably 1 to 6 carbon atoms,
$R^2$ is an unsubstituted or substituted hydrocarbon radical having a total of 1 to 10 carbon atoms, preferably 1 to 6, more preferably 1 to 4 carbon atoms, or the group
$NR^1R^2$ is a heterocyclic ring having 3 to 8 ring atoms which is unsubstituted or substituted and contains the nitrogen atom of the group $NR^1R^2$ as ring heteroatom and may also contain one or two further ring heteroatoms from the group consisting of N, O and S, and
Q is H, or a cation like an alkali or alkaline earth metal cation, e.g. Li, Na, K, Mg or Ca or an ammonium- or phosphonium-cation, e.g. $R_4N$, $R_3NH$, $R_2NH_2$, $RNH_3$, $NH_4$, $R_4P$, wherein R are identical or different unsubstituted or substituted hydrocarbon radicals having 1 to 24 carbon atoms, e.g. $C_1$-$C_{18}$-alkyl, $C_2$-$C_{18}$-alkenyl, $C_2$-$C_{18}$-alkynyl or $C_5$-$C_{18}$-cycloalkyl, each of the 4 latter radicals being unsubstituted or substituted by one or more radicals from the group consisting of halogen, $C_6$-$C_{10}$-aryl, $C_1$-$C_4$-alkoxy, $C_1$-$C_4$-haloalkoxy, $C_1$-$C_4$-alkylthio, mono- and di-($C_1$-$C_4$-alkyl)-amino, cyano, azido, formyl, ($C_1$-$C_4$-alkyl)-carbonyl, ($C_1$-$C_4$-alkoxy)-carbonyl, $C_1$-$C_4$-alkylsulfinyl and $C_1$-$C_4$-alkylsulfonyl, or R is phenyl which is unsubstituted or substituted by radicals from the group consisting of halogen, $C_1$-$C_4$-alkyl, $C_1$-$C_4$-alkoxy, $C_1$-$C_4$-haloalkyl, $C_1$-$C_4$-haloalkoxy and nitro.

In a preferred embodiment the present invention relates to compounds of the formula (I), wherein
$R^1$ is $C_1$-$C_6$-alkyl, $C_2$-$C_6$-alkenyl, $C_2$-$C_6$-alkynyl or $C_5$-$C_6$-cycloalkyl, each of the four latter radicals being unsubstituted or substituted by one or more radicals from the group consisting of halogen, $C_1$-$C_4$-alkoxy, $C_1$-$C_4$-haloalkoxy, $C_1$-$C_4$-alkylthio, mono- and di-($C_1$-$C_4$-alkyl)-amino, cyano, azido, formyl, ($C_1$-$C_4$-alkyl)-carbonyl, ($C_1$-$C_4$-alkoxy)-carbonyl, $C_1$-$C_4$-alkylsulfinyl and $C_1$-$C_4$-alkylsulfonyl, or is phenyl which is unsubstituted or substituted by radicals from the group consisting of halogen, $C_1$-$C_4$-alkyl, $C_1$-$C_4$-alkoxy, $C_1$-$C_4$-haloalkyl, $C_1$-$C_4$-haloalkoxy and nitro,
$R^2$ is $C_1$-$C_6$-alkyl, $C_2$-$C_6$-alkenyl, $C_2$-$C_6$-alkynyl or $C_5$-$C_6$-cycloalkyl, each of the four latter radicals being unsubstituted or substituted by one or more radicals from the group consisting of halogen, $C_1$-$C_4$-alkoxy, $C_1$-$C_4$-haloalkoxy, $C_1$-$C_4$-alkylthio, mono- and di-($C_1$-$C_4$-alkyl)-amino, cyano, azido, formyl, ($C_1$-$C_4$-alkyl)-carbonyl, ($C_1$-$C_4$-alkoxy)-carbonyl, $C_1$-$C_4$-alkylsulfinyl and $C_1$-$C_4$-alkylsulfonyl, or the group
$NR^1R^2$ is a heterocyclic ring of 4, 5 or 6 ring atoms which may contain up to two further ring heteroatoms from the group consisting of N and O in the ring and which is unsubstituted or substituted by one or more $C_1$-$C_4$-alkyl radicals, and
Q is H or an alkali or alkaline earth metal cation or an ammonium- or phosphonium-cation, preferably an alkalimetal kation like Li, Na or K.

Preference is given to compounds of the formula (I) wherein
$R^1$ is $C_1$-$C_4$-alkyl, especially methyl or ethyl,
$R^2$ is $C_1$-$C_4$-alkyl, especially methyl or ethyl, and
Q is H, Na or K.

Examples of compounds of the formula (I) are:

N,N-dimethyl 4-nitro-2-sulfobenzamide potassium salt

N,N-dimethyl 4-nitro-2-sulfobenzamide sodium salt

N,N-dimethyl 4-nitro-2-sulfobenzamide

N,N-diethyl 4-nitro-2-sulfobenzamide potassium salt

N,N-diethyl 4-nitro-2-sulfobenzamide sodium salt

N,N-diethyl 4-nitro-2-sulfobenzamide

N,N-methylethyl 4-nitro-2-sulfobenzamide potassium salt

N,N-methylethyl 4-nitro-2-sulfobenzamide sodium salt

N,N-methylethyl 4-nitro-2-sulfo benzamide

In the formula (I) and whenever used in this specification below (including the paragraphs relating to solvents), the radicals alkyl, alkoxy, haloalkyl, haloalkoxy, alkylamino and alkylthio and their unsaturated and/or substituted counterparts may in each case be straight-chain or branched in the carbon framework. Unless indicated specifically, preference is given in the case of these radicals to the lower carbon frameworks, e.g. those having 1 to 4 carbon atoms, or, in the case of unsaturated groups, having 2 to 4 carbon atoms. Alkyl radicals, both alone and in the composite definitions such as alkoxy, haloalkyl, etc., are for example methyl, ethyl, n-propyl, isopropyl, n-butyl isobutyl, tert-butyl or 2-butyl, pentyls, hexyls, such as n-hexyl, isohexyl and 1,3-dimethylbutyl, and heptyls, such as n-heptyl, 1-methylhexyl and 1,4-dimethylpentyl; alkenyl and alkynyl radicals have the meaning of the possible unsaturated radicals corresponding to the alkyl radicals; alkenyl is for example allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is for example propargyl, but-2-yn-1-yl; but-3-yn-1-yl, 1-methylbut-3-yn-1-yl.

Halogen is for example fluorine, chlorine, bromine or iodine. Haloaryl, haloalkyl, haloalkenyl and haloalkynyl are aryl, alkyl, alkenyl and, respectively, alkynyl which are partially or completely substituted by halogen, preferably by fluorine, chlorine and/or bromine, in particular by fluorine or chlorine, examples being $CF_3$, $CHF_2$, $CH_2F$, $CF_3CF_2$, $CH_2FCHCl$, $CCl_3$, $CHCl_2$, $CH_2CH_2Cl$; haloalkoxy is for example $OCF_3$, $OCHF_2$, $OCH_2F$, $CF_3CF_2O$, $OCH_2CF_3$ and $OCH_2CH_2Cl$; corresponding comments apply to haloalkenyl and other halogen-substituted radicals.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl, preferably alkyl, alkenyl or alkynyl having up to 12 carbon atoms or cycloalkyl having 5 or 6 ring atoms, or phenyl; corresponding comments apply to a hydrocarbonoxy radical.

A heterocyclic radical or ring can be saturated, unsaturated or heteroaromatic; it contains one or more ring heteroatoms, preferably from the group consisting of N, O and S; it preferably has 5 or 6 members and contains 1, 2 or 3 ring heteroatoms. The radical may for example be a heteroaromatic radical or ring (heteroaryl) as defined above, or is a partially hydrogenated radical such as oxiranyl, pyrrolidinyl, piperidyl, piperazinyl, dioxolanyl, morpholinyl, and tetrahydrofuryl. Suitable substituents for a substituted heterocyclic radical are those mentioned below, and also oxo. The oxo group may also be on the ring heteroatoms, which may exist in various oxidation states in the case, for example, of N and S.

Substituted radicals, such as substituted hydrocarbon radicals, e.g. substituted alkyl, alkenyl, alkynyl, aryl, phenyl and benzyl, or substituted heteroaryl, a substituted bicyclic radical or ring or a substituted bicyclic radical, with or without aromatic components, are for example a substituted radical derived from the unsubstituted parent structure, the substituents being for example one or more, preferably 1, 2 or 3, radicals from the group consisting of halogen, alkoxy, haloalkoxy, alkylthio, hydroxyl, amino, nitro, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl and, in the case of cyclic radicals, also alkyl and haloalkyl and unsaturated aliphatic radicals corresponding to the saturated hydrocarbon-containing radicals mentioned, such as alkenyl, alkynyl, alkenyloxy, alkynyloxy, etc. In the case of radicals containing carbon atoms, preference is given to those having 1 to 4 carbon atoms, especially 1 or 2 carbon atoms. In general, preference is given to substituents from the group consisting of halogen, e.g. fluorine and chlorine, $C_1$-$C_4$-alkyl, preferably methyl or ethyl, $C_1$-$C_4$-haloalkyl, preferably trifluoromethyl, $C_1$-$C_4$-alkoxy, preferably methoxy or ethoxy, $C_1$-$C_4$-haloalkoxy, nitro and cyano. In this context, the substituents methyl, methoxy and chlorine are particularly preferred.

Aryl is a mono-, bi- or polycylic aromatic system such as phenyl, naphtyl, indenyl or fluorenyl, preferably phenyl. Substituted or unsubstituted phenyl is preferably phenyl which is unsubstituted or is substituted one or more times, preferably up to three times, by identical or different radicals from the group consisting of halogen, $C_1$-$C_4$-alkyl, $C_1$-$C_4$-alkoxy, $C_1$-$C_4$-haloalkyl, $C_1$-$C_4$-haloalkoxy and nitro, examples being o-, m- and p-tolyl, dimethylphenyls, 2-, 3- and 4-chlorophenyl, 2-, 3- and 4-trifluoro- and -trichlorophenyl, 2,4-, 3,5- 2,5- and 2,3-dichlorophenyl, and o-, m- and p-methoxyphenyl.

An acyl radical is the radical of an organic acid, for example the radical of a carboxylic acid, and radicals of acids derived therefrom, such as of thiocarboxylic acid, of unsubstituted or N-substituted iminocarboxylic acids, or is a radical of carbonic acid monoesters, of unsubstituted or N-substituted carbamic acid, sulfonic acids, sulfinic acids, phosphonic acids, phosphinic acids. Acyl is for example formyl, alkylcarbonyl such as ($C_1$-$C_4$-alkyl)-carbonyl, phenylcarbonyl, where the phenyl ring can be substituted, for example, as shown above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

When used in the description of the various processes set forth below the terms amide, phase transfer catalyst, tertiary amine, activation reagent and acylation reagent include the following meanings.

The term amide among others includes amides such as: dimethyl formamide, diethyl formamide, dimethyl acetamide, N-methyl formanilide, N-methyl acetanilide, 4-formyl morpholine, N-formyl piperidine, N-formyl pyrolidine or mixtures thereof.

The term phase transfer catalyst among others includes ammonium or phosphonium compounds preferably hydrocarbylammonium or hydrocarbylphosphonium compounds such as:

tetraalkylammonium such as tetrabutylammonium, tetraethylammonium, tetramethylammonium, cetyltrimethylammonium or methyltrioctylammoniumchloride (Alliquat® 336), benzyltriethylammonium, benzyltrimethylammonium, or tetraphenylphosphonium, each as chloride, bromide, hydrogensulfate, sulfate or mixtures thereof.

The term tertiary amine among others includes alkylamines such as:

triethylamine, tributylamine, benzyldialkylamine, N-alkylmorpholine, N-alkylpiperidine, N-alkylpyrrolidine, or aromatic amines such as pyridine, 2 or 3 or 4-methylpyridine, 2,3 or 2,4 or 2,5 or 2,6 or 3,4 or 3,5-dimethylpyridine, N,N-dialkylaniline, e.g. N,N-dimethylaniline, or mixtures thereof.

The term activation reagent means a reagent that is capable of converting an acid into the acid-chloride or acid-anhydride or similarly reactive derivatives of the acid, and amongst others includes phosgene, thionyl chloride, phosphorous oxychloride, phosphorous trichloride, phosphorous pentachloride, sulfonyl chloride, or mixtures thereof.

The term acylation reagent means a reagent that is capable of substituting hydrogen by an acyl radical and among others includes formic acid and $C_1$-$C_8$-carboxylic acid anhydrides, e.g. acetic anhydride or formic acetic anhydride.

With regard to the description of the various process set forth below, the chemical classes of solvents mentioned therein include the following meanings.

The term aryl among others includes nitrobenzene, toluene, xylene, chlorobenzene and dichlorobenzene. The term alkyl among others includes pentane, hexane, dichloromethane and dichloroethane. The term ester among other includes ethylacetate, propylacetate and butylacetate. The term ether among others includes dibutylether, dipropylether, dioxane and tetrahydrofurane. The term nitrile among others includes acetonitrile, propionitrile and benzonitrile. The term carboxylic acid among others includes formic acid, acidic acid, propionic acid and butyric acid. The term carbonate among others includes diethylcarbonate. The term amide among others includes N-methylpyrolidone, dimethylformamide and dimethylacetamide. The term sulfone among others includes dimethylsulfone. The term ketone among others includes acetone, ethylmethylketone, diethylketone and cyclohexanone. The term carbamate among others include trimethylcarbamate. The term alcohol among others includes methanol, ethanol, propanol and butanol.

The benzamides of the formula (I) of the present invention can be obtained for example by reaction of the appropriately substituted amine of the formula NHR$^1$R$^2$ or a salt thereof wherein R$^1$ and R$^2$ are defined as in formula (I), with the anhydride of the formula (II).

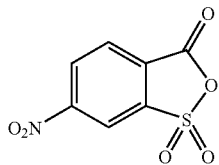

(II)

Reaction of the anhydride of the formula (II) with between 1 and 10 equivalents, preferably 1 and 4 equivalents and especially 1 to 2 equivalents of an appropriately substituted amine (NHR$^1$R$^2$) affords in the presence or preferably in the absence of a tertiary amine the desired benzamides of the formula (I) in excellent yields. The reaction may be carried out at temperatures between about −50 and 300° C., preferably −20 and 180° C., in solvents or mixtures of solvents such as but not limited to unsubstituted or substituted hydrocarbones such as unsubstituted or substituted aryls (e.g. alkylaryls or haloaryls) or unsubstituted or substituted alkyls (e.g. haloalkyls), esters and ethers, at atmospheric, reduced or increased pressure.

The anhydride of the formula (II) can be obtained e.g. according to Helv. Chim. Acta, 1949, 32, 172 by reaction of the:

a) dipotassium 4-nitro-2-sulfobenzoate of the formula (III), wherein Q$^1$=Q$^2$=K, with phosphorous pentachloride in substance, or b) potassium 4-nitro-2-sulfobenzoate of the formula (III), wherein Q$^1$=H, Q$^2$=K, with thionyl chloride in substance, or c) 4-nitro-2-sulfobenzoic acid of the formula (III), wherein Q$^1$=Q$^2$=H with acetyl chloride at reflux, by distillation at about 184° C. or with phosphorous pentoxide as a melt.

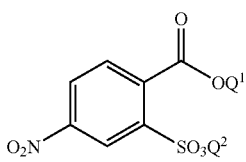

(III)

The anhydride of the formula (II) can also be obtained from the reaction of the diacid of the formula (III) with possibly up to 4 equivalents, preferably 1 to 2 equivalents of an activation reagent, preferably thionyl chloride or phosgene, possibly in the presence of a phase transfer catalyst, preferably benzyltriethylammonium chloride, and optionally in the presence an amide catalyst, preferably dimethyl formamide, and optionally in the presence a tertiary amine catalyst, preferably pyridine. Thereafter of the excess reagent is removed by, for example but not limited to, distillation at or above atmospheric pressure or under vacuum. The reaction may carried out, in solvents or mixtures of solvents such as but not limited to: unsubstituted or substituted hydrocarbones such as unsubstituted or substituted aryls (e.g. alkylaryls or haloaryls) or unsubstituted or substituted alkyls (e.g. haloalkyls), carbonates, carbamates, esters, ethers, and sulfones, at, above or below their boiling point at atmospheric, reduced or increased pressure, at temperatures between about 0° C. to 300° C., preferably between 40° C. to 150° C.

Surprisingly it was found that the anhydride of the formula (II) can also be obtained by reaction of a dichloride of the formula (IV) with a diacid of the formula (III). In this reaction the dichloride of the formula (IV) (or other doubly activated isomers or derivatives thereof such as disclosed in DE 2616611, see e.g. formula (V) therein) may, after removal of excess reagent by, for example but not limited to, distillation at or above atmospheric pressure or under vacuum, be reacted with fresh diacid of the formula (III) or a salt thereof, other carboxylic acids (RCO$_2$H, where R is C$_1$-C$_8$-alkyl), or other molecules capable of supplying the necessary oxygen atom, such as sulfoxides or tertiary N-oxides, optionally in the presence of a tertiary amine, preferably pyridine. The reaction may be carried out in solvents or mixtures of solvents such as but not limited to: unsubstituted or substituted hydrocarbones such as unsubstituted or substituted aryls (e.g. alkylaryls or haloaryls) or unsubstituted or substituted alkyls (e.g. haloalkyls), carbonates, carbamates, amides, esters, ethers, nitriles and sulfones, at, above or below their boiling point at atmospheric, reduced or increased pressure, at temperatures between about 0° C. to 300° C., preferably between 40° C. to 150° C., to produce the anhydride of the formula (II) in excellent yield.

The dichloride of the formula (IV) (or other doubly activated isomers or derivatives thereof such as disclosed in DE 2616611, see e.g. formula (V) therein) can be obtained e.g. by reaction of the free diacid of the formula (III) (Q$^1$=Q$^2$=H) or dipotassium salt of the formula (III) (Q$^1$=Q$^2$=K) with thionyl chloride or phosgene in the presence of amide catalyst, preferably dimethyl formamide (see eg. DE 2616611).

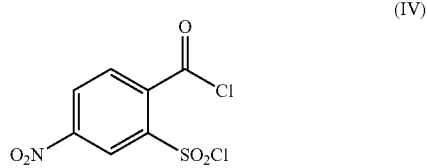

(IV)

Surprisingly the benzamides of the formula (I) of the present invention can also be obtained by direct reaction of a diacid of the formula (III) or a salt thereof,

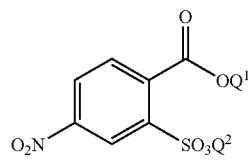

(III)

where in Q$^1$ and Q$^2$ are identical or different and are H or a cation like an alkali or alkaline earth metal cation, e.g. Li, Na, K, Mg or Ca or an ammonium- or phosphoniumcation, e.g. R$_4$N, R$_3$NH, R$_2$NH$_2$, RNH$_3$, NH$_4$, R$_4$P, wherein R are identical or different unsubstituted or substituted hydrocarbon radicals having 1 to 24 carbon atoms, e.g. C$_1$-C$_{18}$-alkyl, C$_2$-C$_{18}$-alkenyl, C$_2$-C$_{18}$-alkynyl or C$_5$-C$_{18}$-cycloalkyl, each of the 4 latter radicals being unsubstituted or substituted by one or more radicals from the group consisting of halogen, C$_6$-C$_{10}$-aryl, C$_1$-C$_4$-alkoxy, C$_1$-C$_4$-haloalkoxy, C$_1$-C$_4$-alkylthio, mono- and di-(C$_1$-C$_4$-alkyl)-amino, cyano, azido, formyl, (C$_1$-C$_4$-alkyl)-carbonyl, (C$_1$-C$_4$-alkoxy)-carbonyl, C$_1$-C$_4$-alkylsulfinyl and C$_1$-C$_4$-alkylsulfonyl, or R is phenyl which is unsubstituted or substituted by radicals from the group consisting of halogen, C$_1$-C$_4$-alkyl, C$_1$-C$_4$-alkoxy, C$_1$-C$_4$-haloalkyl, C$_1$-C$_4$-haloalkoxy and nitro, with an appropriately substituted amine or a salt thereof, in the presence of an activation reagent, preferably thionylchloride.

The reaction is carried out optionally in the presence of a phase transfer catalyst, preferably benzyltriethylammonium chloride, and optionally in the presence of a tertiary amine catalyst. The reaction may be carried out in substance or in solvents such as but not limited to unsubstituted or substituted hydrocarbones such as unsubstituted or substituted aryls (e.g. alkylaryls or haloaryls) or unsubstituted or substituted alkyls (e.g. haloalkyls), carbonates, carbamates, esters, ethers, nitriles and sulfones, at, above or below their boiling point at atmospheric, reduced or increased pressure, at temperatures between about 0° C. to 300° C., preferably between 40° C. to 150° C., and renders the benzamides of the formula (I) in excellent yields.

The benzamides of the formula (I) may be isolated by techniques commonly practised in the laboratory and known to those skilled in the art such as filtration, or they may be further reacted without isolation. The benzamides of the formula (I) are valuable intermediates for the preparation of various products such as sulfonylareas intended for use in crop protection.

For example, by hydrogenation the nitrobenzamides of the formula (I) can be converted into the corresponding aminobenzamides of the formula (V), wherein Q, R$^1$ and R$^2$ are defined as in formula (I). The hydrogenation may be carried out with hydrogen or a hydrogen source such as cyclohexadiene, in the presence of a metal catalyst like: Pd/C, Pt/C, Ru/C or Raney-Ni alone or in combination, possibly in the presence of other metal derivatives such as the oxides of or the salts of the metals manganese, molybdenum, tungsten, iron and cobalt in which the metal is present as cation, oxoanion or polyoxoanion, in an inert solvent or solvent mixture thereof, such as but nor limited to: water, alcohols, ethers, carboxylic acids and ketones, alone or as mixtures, or as mixtures with the solvents used in the preparation of the benzamides of the formula (I), at temperatures between about −30° C. to 300° C. and preferably between −10° C. and 150° C.

The benzamides of the formula (I) may also be hydrogenated and subsequently or simultaneously (reductive acylation) be reacted with an acylating reagent. For instance the benzamides of the formula (I) may be reacted with hydrogen or a hydrogen source such as cyclohexadiene, in the presence of a) a metal catalyst like: Pd/C, Pt/C, Ru/C or Raney-Ni alone or in combination, possibly in the presence of other metal derivatives such as the oxides of or the salts of the metals manganese, molybdenum, tungsten, iron and cobalt in which the metal is present as cation, oxoanion or polyoxoanion, and b) an acylating agent such as formic acid and/or an C$_1$-C$_8$-carboxylic acid anhydride, optionally in other solvents or mixture of solvents, such as but not limited to: alkylaryl, aryl, carbonate, carbamate, ester, ether, haloalkyl, haloaryl, ketone, nitrile, sulfones and water or an inert solvent or solvent mixture, such as but not limited to: unsubstituted or substituted hydrocarbones such as unsubstituted or substituted aryls (e.g. alkylaryls or haloaryls) or unsubstituted or substituted alkyls (e.g. haloalkyls), carbonates, carbamates, esters, ethers, ketones, nitrites and sulfones, at temperatures between about −30° C. to 300° C. and preferably between −10° C. and 150° C., to form the corresponding acylamido derivatives of the formula (VI), where Q, R$^1$ and R$^2$ are defined in formula (I) and A is an acyl radical, preferably a formyl radical or a C$_1$-C$_8$-hydrocarbyl-carbonyl radical, such as a branched or straight chain C$_1$-C$_8$-alkyl-carbonyl radical.

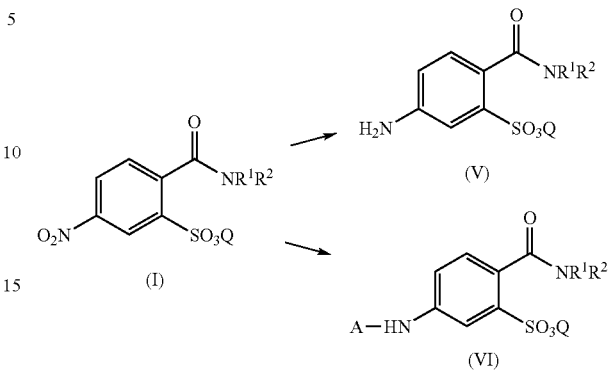

The benzamide of the formula (I) may be reacted with an activation reagent, preferably thionyl chloride or phosgene, in the presence of an amide catalyst, preferably dimethyl formamide, optionally in the presence of a phase transfer catalyst, preferably benzyltriethylammonium chloride, and optionally in the presence of a tertiary amine catalyst, preferably pyridine, to form in excellent yields the sulfonyl chlorides of the formula (VII), where R$^1$ and R$^2$ are defined as in formula (I). Thereafter the excess reagent is removed by, for example but not limited to: distillation at or above atmospheric pressure or under vacuum, in solvents such as but not limited to unsubstituted or substituted hydrocarbones such as unsubstituted or substituted aryls (e.g. alkylaryls or haloaryls) or unsubstituted or substituted alkyls (e.g. haloalkyls), esters, carbonates and ethers, at or below their boiling point at atmospheric, reduced or increased pressure, at temperatures between about 0° C. to 200° C., preferably between 50° C. and 150° C.

The compound of the formula (VII) may be isolated by techniques commonly practiced in the laboratory and to those skilled in the art such as filtration. The sulfonyl chlorides of the formula (VII) may also be further reacted, preferably without further isolation at temperatures between about −100° C. to 200° C., preferably −30° C. to 100° C. with ammonia, primary or secondary amines, optionally in the presence of a tertiary amine, preferably pyridine, to give in excellent yields the corresponding sulfonamides of the formula (VIII), where R$^1$ and R$^2$ are defined as in formula (I) and where R$^4$ and R$^5$ are hydrogen or C$_1$-C$_{12}$-hydrocarbon radical like straight or branched chain C$_1$-C$_{12}$-alkyl, C$_1$-C$_{12}$-alkenyl or C$_1$-C$_{12}$-alkynyl, C$_6$-C$_{12}$-aryl or heteroaryl, where the ring or chain may contain one or more of the following substituents or functional groups: acyloxy, amido, aminosulfonyl, aryl, heteroaryl, aryloxy, heteroaryloxy, carbonylamino, dialkylamino, ether, ester, halo, nitrile, nitro, sulfonamido, akylmercapto, arylmercapto, heteroarylmercapto, where R$^4$ may or may not be identical to R$^5$.

The sulfonyl chlorides of the formula (VII) may also be reacted with cyanate salts (e.g. MOCN, where M is a cation like an alkali or alkaline earth metal cation, such as Li, Na, K, Mg or Ca or an ammonium- or phosphoniumcation), possibly in the presence of a phase transfer catalyst (including in addition to those previously described polyethylene, glycols and polyethers), and optionally in the presence of a tertiary amine catalyst, preferably pyridine, triethylamine or tributylamine, or mixtures thereof, at temperatures between about −100° C. to 150° C., preferably −30° C. to 100° C. to form in excellent yields the sulfonyl isocyanates of the formula (IX-A) or (IX-B), where $R^1$ and $R^2$ are defined as in formula (I) and Z in formula (IX-B) is a tertiary ammonium radical obtained from a tertiary amine as defined above, such as pyridinium, tributylammonium or triethylammonium. The sulfonyl isocyanate of the formula (IX-B) may be obtained if the reaction is carried out in the presence of a nucleophilic tertiary amine catalyst.

The isocyanate of the formula (IX-A) or (IX-B) where $R^1$ and $R^2$ are defined as in formula (I) and Z in formula (IX-B) is a tertiary ammonium radical obtained from a tertiary amine as defined above such as pyridinium, tributylammonium or triethylammonium may also be prepared by the reaction of the sulfonamides of the formula (VIII) wherein $R^4=R^5=H$ with phosgene, optionally in the presence of a tertiary amine catalyst preferably pyridine, triethylamine or tributylamine, or mixtures thereof, at a temperature between about $-100°$ C. to $150°$ C., preferably $-30°$ C. to $100°$ C. The sulfonyl isocyanate of the formula (IX-B) may be obtained if the reaction is carried out in the presence of a nucleophilic tertiary amine catalyst.

used in the preparation of the sulfonamides of the formula (VIII), at temperatures between about $-30°$ C. to $300°$ C. and preferably between $-10°$ C. and $150°$ C.

The sulfonamides of the formula (VIII) may also be hydrogenated and subsequently or simultaneously (reductive acylation) be reacted with an acylating reagent. For instance the sulfonamides of the formula (VIII) may be reacted with hydrogen or a hydrogen source such as cyclohexadiene in the presence of a) a metal catalyst like: Pd/C, Pt/C, Ru/C or Raney-Ni alone or in combination, possibly in the presence of other metal derivatives such as the oxides of or the salts of the metals manganese, molybdanum, tungsten, iron and cobalt in which the metal is present as cation, oxoanion or polyoxoanion, and b) an acylating reagent such as formic acid and/or an $C_1$-$C_8$-carboxylic acid anhydride, optionally in other solvents or mixture of solvents, such as but not limited to: unsubstituted or substituted hydrocarbones such as unsubstituted or substituted aryls (e.g. alkylaryls or haloaryls) or unsubstituted or substituted alkyls (e.g. haloalkyls), carbonates, carbamates, esters, ethers, ketones, nitriles and sulfones, at temperatures between about $-30°$ C. to $300°$ C. and preferably

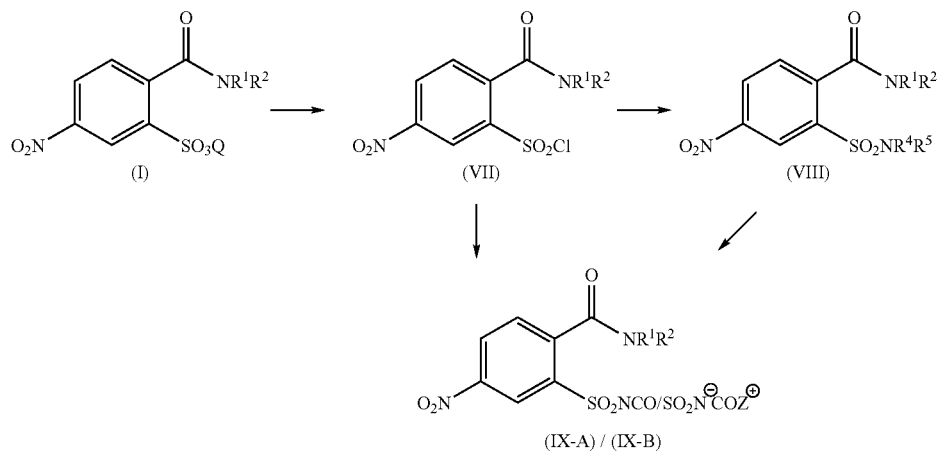

The sulfonamides of the formula (VIII) may be isolated by techniques commonly practised in the laboratory and known to those skilled in the art such as filtration or they may be further reacted without isolation. The sulfonamides of the formula (VIII) are valuable intermediates for the preparation of various products such as sulfonylareas intended for use in crop protection.

For example, by hydrogenation the sulfonamides of the formula (VIII) can be converted into the corresponding sulfonamides of the formula (V*), wherein $R^1$, $R^2$, $R^4$ and $R^5$ are defined as in formula (VIII). The hydrogenation may be carried out with hydrogen or a hydrogen source such as cyclohexadiene in the presence of a metal catalyst like: Pd/C, Pt/C, Ru/C or Raney-Ni alone or in combination, possibly in the presence of other metal derivatives such as the oxides of or the salts of the metals manganese, molybdanum, tungsten, iron and cobalt in which the metal is present as cation, oxoanion or polyoxoanion, in an inert solvent or solvent mixture thereof, such as but nor limited to: water, alcohols, unsubstituted or substituted hydrocarbones such as unsubstituted or substituted aryls (e.g. alkylaryls or haloaryls) or unsubstituted or substituted alkyls (e.g. haloalkyls), ethers, carbonates, carbamates, esters, nitrites, sulfones, carboxylic acids and ketones, alone or as mixtures, or as mixtures with the solvents between $-10°$ C. and $150°$ C., to form the corresponding acylamido derivatives of the formula (VI*), where $R^1$, $R^2$, $R^4$ and $R^5$ are defined as in formula (VIII) and A is an acyl radical, preferably a formyl radical or a $C_1$-$C_8$ hydrocarbylcarbonyl radical, such as a branched or straight chain $C_1$-$C_8$-alkyl-carbonyl radical

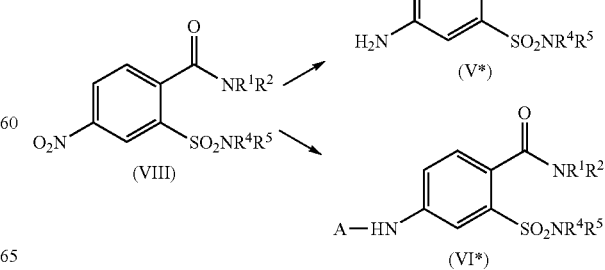

The sulfonamide of the formula (VIII) and the sulfonyl isocyanates of the formula (IX-A) and (IX-B) can be advantageously used to prepare in excellent yields sulfonylureas which exhibit herbicidal activity. Examples of herbicidal sulfonylareas are sulfonylureas of the formulas (XII) and (XIV) below, such as N-(4,6-dimethoxypyrimidin-2-ylaminocarbonyl)-2-(N,N-dimethylaminocarbonyl)-5-(N-methoxycarbonylamino)benzenesulfonamide, N-(4,6-dimethoxypyrimidin-2-ylaminocarbonyl)-2-(N,N-dimethylaminocarbonyl)-5-(N-propionyl-amino)benzenesulfonamide sodium salt, N-(4,6-dimethoxypyrimidin-2-ylaminocarbonyl)-2-(N,N-dimethylaminocarbonyl)-5-(N-formylamino)benzenesulfonamide, N-(4,6-dimethoxypyrimidin-2-ylaminocarbonyl)-2-(N,N-dimethylaminocarbonyl)-5-(N-formylamino)benzenesulfonamide sodium salt or N-(4,6-dimethoxypyrimidin-2-ylaminocarbonyl)-2-(N,N-dimethylaminocarbonyl)-5-(N-methoxycarbonylamino)benzenesulfonamide. The sulfonylareas can form salts where the hydrogen of the —$SO_2$—NH— group is replaced by an agriculturally suitable cation. These salts are, for example, metal salts, in particular alkali metal salts or alkaline-earth metal salts, in particular sodium salts and potassium salts, or else ammonium salts or salts with organic amines. Likewise, salt formation can be carried out by adding an acid to basic groups, such as, for example, amino and alkylamino. Suitable acids for this purpose are strong inorganic and organic acids, for example HCl, HBr, $H_2SO_4$ or $HNO_3$.

For example the sulfonamide of the formula (VIII) can be reacted as described above α) with hydrogen or a hydrogen source such as cyclohexadiene in the presence of a metal catalyst and optionally an acylating reagent such as formic acid or $C_1$-$C_8$-carboxylic acid anhydrides optionally in the presence of a solvent or mixture of solvents such as but not limited to alkylaryl, amide, aryl, ester, ether, haloalkyl, haloaryl, nitrile, alcohol, ketone, carbonylic acids or mixtures of these solvents with water, at a temperature of for example about 0°-250° C., at a pressure of for example 1-200 bar, to give a compound of the formula (A) (formula (A) encompasses formula (V*) and (VI*))

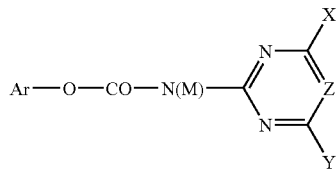

(A)

wherein $R^1$ and $R^2$ are defined as in formula (I), $R^4$ and $R^5$ are hydrogen or a $C_1$-$C_{12}$-hydrocarbon radical and A* is hydrogen or an acyl radical, and then reacting the compound of the formula (A) previously obtained with i) a compound of the formula (X)

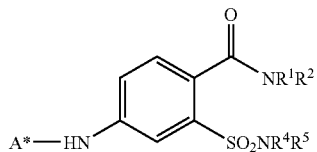

(X)

wherein

Ar is unsubstituted or substituted phenyl,

M is H, $C_1$-$C_4$-alkyl or a metal cation,

X and Y independently of one another are halogen, $C_1$-$C_6$-alkyl, $C_1$-$C_6$-alkoxy, $C_1$-$C_6$-alkylthio, each of the three latter radicals being unsubstituted or substituted by one or more radicals from the group consisting of halogen, $C_1$-$C_4$-alkoxy and $C_1$-$C_4$-alkylthio, or are $C_3$-$C_6$-cycloalkyl, $C_2$-$C_6$-alkenyl, $C_2$-$C_6$-alkynyl, $C_3$-$C_6$-alkenyloxy or $C_3$-$C_6$-alkynyloxy, and Z is CH or N, at a temperature of for example about −50-150° C., at atmospheric, reduced or increased pressure, optionally in the presence of a solvent or mixture of solvents such as but not limited to unsubstituted or substituted hydrocarbones such as unsubstituted or substituted aryls (e.g. alkylaryls or haloaryls) or unsubstituted or substituted alkyls (e.g. haloalkyls), esters, ethers, amides, nitriles and ketones, and optionally in the presence of a base such as but not limited to carbonates, alkoxides, hydroxides or tertiary amines, or ii) a compound of the formula (XI)

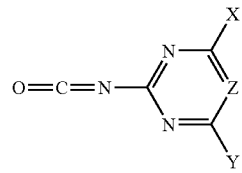

(XI)

wherein

X and Y independently of one another are halogen, $C_1$-$C_6$-alkyl, $C_1$-$C_6$-alkoxy, $C_1$-$C_6$alkylthio, each of the three latter radicals being unsubstituted or substituted by one or more radicals from the group consisting of halogen, $C_1$-$C_4$-alkoxy and $C_1$-$C_4$-alkylthio, or are $C_3$-$C_6$-cycloalkyl, $C_2$-$C_6$-alkenyl, $C_2$-$C_6$-alkynyl, $C_3$-$C_6$-alkenyloxy or $C_3$-$C_6$-alkynyloxy, and Z is CH or N, at a temperature of for example about −50-150° C., at atmospheric, reduced or increased pressure, optionally in the presence of a solvent or mixture of solvents such as but not limited to unsubstituted or substituted hydrocarbones such as unsubstituted or substituted aryls (e.g. alkylaryls or haloaryls) or unsubstituted or substituted alkyls (e.g. haloalkyls), esters, ethers and nitrites, to give a sulfonylarea of the formula (XIV) or a salt thereof

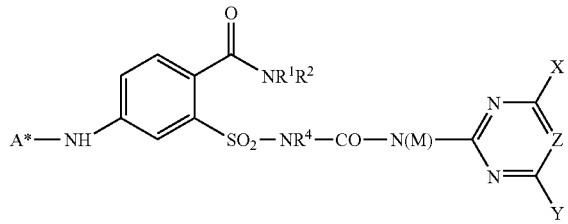

(XIV)

wherein $R^1$, $R^2$ and $R^4$ are defined as in formula (VIII) and M, X, Y and Z are defined as in formula (X) and A* is hydrogen or an acyl group.

The sulfonamide of the formula (VIII) can also be reacted
β) as described in WO 97/16419 which is fully herewith incorporated by reference with a compound of the formula (X)

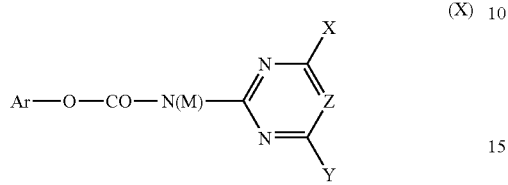
(X)

wherein
Ar is unsubstituted or substituted phenyl,
M is H, $C_1$-$C_4$-alkyl or a metal cation,
X and Y independently of one another are halogen, $C_1$-$C_6$-alkyl, $C_1$-$C_6$-alkoxy, $C_1$-$C_6$-alkylthio, each of the three latter radicals being unsubstituted or substituted by one or more radicals from the group consisting of halogen, $C_1$-$C_4$-alkoxy and $C_1$-$C_4$-alkylthio, or are $C_3$-$C_6$-cycloalkyl, $C_2$-$C_6$-alkenyl, $C_2$-$C_6$-alkynyl, $C_3$-$C_6$-alkenyloxy or $C_3$-$C_6$-alkynyloxy, and
Z is CH or N, or
γ) as described in WO 95/29899 (=EP-A-757679) which is fully incorporated herewith by reference with a compound of the formula (XI)

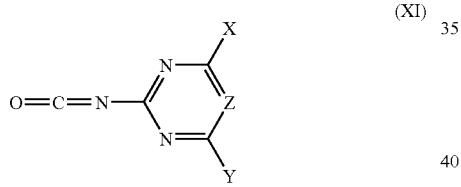
(XI)

wherein
X and Y independently of one another are halogen, $C_1$-$C_6$-alkyl, $C_1$-$C_6$-alkoxy, $C_1$-$C_6$-alkylthio, each of the three latter radicals being unsubstituted or substituted by one or more radicals from the group consisting of halogen, $C_1$-$C_4$-alkoxy and $C_1$-$C_4$-alkylthio, or are $C_3$-$C_6$-cycloalkyl, $C_2$-$C_6$-alkenyl, $C_2$-$C_6$-alkynyl, $C_3$-$C_6$-alkenyloxy or $C_3$-$C_6$-alkynyloxy, and
Z is CH or N, or
δ) as described in WO 00/05220 which is fully incorporated herewith by reference with an activation reagent such as phosgene and an amine to give a compound of the formula (IX-A) or (IX-B)

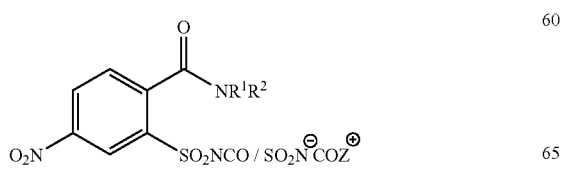
(IX-A)/(IX-B)

wherein $R^1$ and $R^2$ are defined as in formula (I) in claim 1 to 3, and then reacting the compound of the formula (IX) previously obtained with a compound of the formula (XI*)

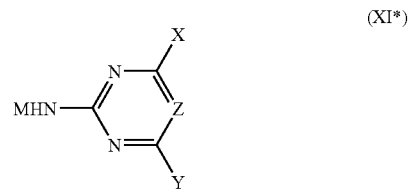
(XI*)

wherein M is H, $C_1$-$C_4$-alkyl or a metal cation,
X and Y independently of one another are halogen, $C_1$-$C_6$-alkyl, $C_1$-$C_6$-alkoxy, $C_1$-$C_6$-alkylthio, each of the three latter radicals being unsubstituted or substituted by one or more radicals from the group consisting of halogen, $C_1$-$C_4$-alkoxy and $C_1$-$C_4$-alkylthio, or are $C_3$-$C_6$-cycloalkyl, $C_2$-$C_6$-alkenyl, $C_2$-$C_6$-alkynyl, $C_3$-$C_6$-alkenyloxy or $C_3$-$C_6$-alkynyloxy, and
Z is CH or N,
at a temperature of for example about −50-150° C., at atmospheric, reduced or increased pressure, optionally in the presence of a solvent or mixture of solvent such as but not limited to unsubstituted or substituted hydrocarbones such as unsubstituted or substituted aryls (e.g. alkylaryls or haloaryls) or unsubstituted or substituted alkyls (e.g. haloalkyls), esters, ethers and nitriles,
to give a nitrophenyl-sulfonylurea compound of the formula (XII) or a salt thereof

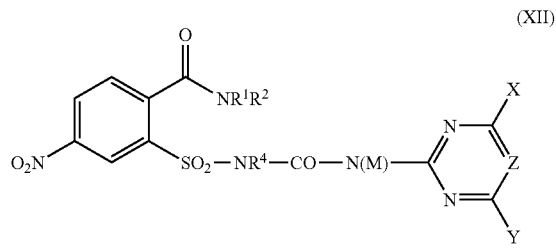
(XII)

wherein $R^1$, $R^2$ and $R^4$ are defined as in formula (VIII) and M, X, Y and Z are defined as in formula (X).

The nitrophenyl-sulfonylureas of the formula (XII) or a salt thereof can be further transformed into the corresponding aminophenyl-sulfonylureas of the formula (XIV) or salts thereof

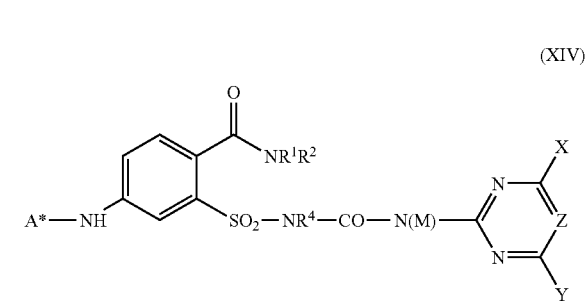
(XIV)

wherein R¹, R² and R⁴ are defined as in formula (VIII) and M, X, Y and Z are defined as in formula (X) and A* is H, by hydrogenation, e.g. as described above for compounds of the formula (I) and (VII) or as described in WO 97/16419 which is herewith fully incorporated by reference.

For example the hydrogenation may be carried out with hydrogen or a hydrogen source such as cyclohexadiene in the presence of a metal catalyst like: Pd/C, Pt/C, Ru/C or Raney-Ni alone or in combination, possibly in the presence of other metal derivatives such as the oxides of or the salts of the metals manganese, molybdanum, tungsten, iron and cobalt in which the metal is present as cation, oxoanion or polyoxoanion, in an inert solvent or solvent mixture thereof, such as but nor limited to: water, alcohols, unsubstituted or substituted hydrocarbones such as unsubstituted or substituted aryls (e.g. alkylaryls or haloaryls) or unsubstituted or substituted alkyls (e.g. haloalkyls), ethers, carbonates, carbamates, esters, nitrites, sulfones, carboxylic acids and ketones, at temperatures between about −30° C. to 300° C. and preferably between −10° C. and 150° C.

The nitrophenyl-sulfonylureas of the formula (XII) or a salt thereof can also be further transformed into the corresponding acylamidophenyl-sulfonylureas of the formula (XIV) of a salt thereof, wherein R¹, R² and R⁴ are defined as in formula (VII) and M, X, Y and Z are defined as in formula (X) and A* is an acyl group, preferably a formyl radical or a $C_1$-$C_8$ hydrocarbyl-carbonyl radical, such as a branched or straight chain $C_1$-$C_8$-alkyl-carbonyl radical, by hydrogenation and subsequent acylation or simultaneous acylation (reductive acylation=hydrogenation in the presence of an acylating reagent), e.g. as described above for the compounds of the formula (I) and (VIII) or as described in WO 97/16419 which is herewith fully incorporated by reference.

For example the reaction may be carried out with hydrogen or a hydrogen source such as cyclohexadiene in the presence of a) a metal catalyst like: Pd/C, Pt/C, Ru/C or Raney-Ni alone or in combination, possibly in the presence of other metal derivatives such as the oxides of or the salts of the metals manganese, molybdenum, tungsten, iron and cobalt in which the metal is present as cation, oxoanion or polyoxoanion, and b) an acylating reagent such as formic acid and/or an $C_1$-$C_8$-carboxylic acid anhydride, optionally in other solvents or mixture of solvents, such as but not limited to: unsubstituted or substituted hydrocarbones such as unsubstituted or substituted aryls (e.g. alkylaryls or haloaryls) or unsubstituted or substituted alkyls (e.g. haloalkyls), carbonates, carbamates, esters, ethers, ketones, nitriles and sulfones, at temperatures between about −30° C. to 300° C. and preferably between −10° C. and 150° C., to form the corresponding acylamidophenyl-sulfonylurea of the formula (XIV) or a salt thereof.

The processes described herein above render in excellent yields herbicidally active sulfonylureas and their prescursors such as sulfochlorides or sulfonamides. The present invention is illustrated by the following examples.

EXAMPLES

Example 1

N,N-Dimethyl 4-nitro-2-sulfobenzamide potassium salt (I)
A) A suspension of 31.9 g 4-nitro-2-sulfobenzoic acid potassium salt (III) in toluene (240 ml) was heated to reflux and 0.6-0.8 ml of water removed azeotropically. The mixture was then cooled to 85-90° C., dimethyl formamide (0.23 ml) and pyridine (0.16 ml added and over 4 hours phosgene (10.1 g) added. After heating for a further 2 hours at 85-90° C. the excess phosgene was removed by blowing nitrogen through the solution. Dimethylamine (4.78 g) was then added at 98-103° C. to the phosgene free solution. After 1 hour the suspension was cooled to 20° C., filtered and the solid displacement washed with toluene (2×20 ml), pressed well and dried at 75° C./50 mbar. Yield: 35.1 g (=90%), 80.1% w/w; mp.: dec. 320° C.

B) A mixture of 4-nitro-2-sulfobenzoic acid potassium salt (50 g), dimethylamine hydrochloride (14.2 g) and tetrabutylammonium bromide (1.0 g) in xylene (120 ml) was heated to 100° C. and thionyl chloride (15 ml) added dropwise over 45 minutes. After 2 hours the reaction is cooled to 20° C., the product filtered and washed with xylene (2×50 ml). Yield: 61.72 g (=91.3%), 70.0% w/w.

Example 2

N, N-Dimethyl 2-aminosulfonyl-4-nitrobenzamide (VIII)

A) A suspension of 79.9 g 4-nitro-2-sulfobenzoic acid potassium salt (I) in xylene (570 ml) was heated to 88-92° C., dimethyl formamide (1 ml) added, and phosgene (58 g) added as a gas over 3 hours. After a further 1 hour the excess phosgene was removed by distillation and a second charge of 4-nitro-2-sulfobenzamide potassium salt (75.7 g) and pyridine (0.6 ml) added. The mixture was then heated to 138° C. for 1 hour, cooled to 95-100° C. and dimethylamine (23.5 g) added over 2 hours and the mixture heated for 30 minutes at this temperature. The suspension was then cooled to 70-75° C. and in 2 hours a solution of dimethyl formamide (0.38 ml) in xylene (10 ml) and phosgene (77.1 g) added. The excess phosgene was then after 1 hour removed by distillation and the reaction cooled to 0-5° C. At this point ammonia (19.5 g) was added so that the temperature remained below 5° C. Finally the mixture was warmed to 20° C., water (420 ml) and conc. sulfuric acid (7.4 g) (final pH=4) added and the mixture stirred for 15 minutes. The solid was filtered washed with water (5×100 ml), pressed well and dried at 75° C./50 mbar. Yield 111.4 g (=81%), 93.4% w/w.

B) A mixture of 31.9 g 4-nitro-2-sulfobenzoic acid potassium salt (II) and toluene (240 ml) was heated to reflux and 0.6-0.8 ml of water removed azeotropically. The mixture was then cooled to 82-87° C., benzyltriethylammonium chloride (0.91 g) added and over two hours thionyl chloride (9.2 ml) added dropwise. After a further hour a mixture of toluene and thionyl chloride (25 ml) was removed by distillation and between 95-100° C. dimethylamine (7.5 g) added as a gas. Following 1 hour at this temperature the mixture is cooled to 70-75° C. and in 2 hours dimethyl formamide (0.08 ml) as a solution in toluene (2 ml) and phosgene (15.8 g) added. 1 Hour later the phosgene was removed by blowing nitrogen through the mixture and at 0-5° C. ammonia (4 g) added. After warming under vacuum to 40° C. the product was isolated by filtration, washed with toluene (3×20 ml) and pressed well. The solid was then re-suspended in water (85 ml) and acetone (2.5 ml), stirred, filtered washed with water (5×20 ml) and finally dried at 75° C./50 mbar. Yield 23.6 g (=82%), 95.6% w/w mp.: 161-162° C.

Example 3

N,N-Dimethyl 2-aminosulfonyl-4-formamidobenzamide (VI*)

A suspension of 40 g N,N-Dimethyl 2-aminosulfonyl-4-nitrobenzamide (VIII), sodium molybdate (0.08 g) and Pd/C (3 g, 5%, 50% water) in formic acid (200 ml) was hydrogenated at 50° C. and 40 bar for 7 hours. The catalyst was then filtered and washed with formic acid (20 ml). The filtrate was concentrated in vacuo and ethyl acetate (200 ml) added. After stirring for 2 hours at 20° C. the product was filtered, the filtrate concentrated and re-filtered. The combined solids were washed with ethyl acetate (20 ml) and dries at 50° C./50 mbar. Yield: 35.3 g (=84.3%), 94.1% w/w, mp.: 192-193° C.

Example 4

N,N-Dimethyl 2-(N—(N-(4,6-dimethoxypyrimid-2-yl)-aminocarbonyl)-aminosulfonyl)-4-nitrobenzamide (XII)

To a solution of phosgene (20 g) in ethyl acetate (70 ml) at 0° C. in 2.5 hours was added a mixture of 20 g N,N-dimethyl 2-aminosulfonyl-4-nitrobenzamide (VIII)) and triethylamine (39 ml) in ethyl acetate (200 ml). After 30 minutes the excess phosgene is removed by blowing nitrogen through the mixture and a solution from 2-amino-4,6-dimethoxypyrimidine (11.9 g) in ethyl acetate (80 ml) added dropwise. After a further 1.5 hours water (200 ml) and potassium hydroxide (5N, 45 ml) was added and after clarification the phases separated. The organic phase was extracted with water (2×50 ml) and the combined aqueous phases acidified to pH=2 with hydrochloric acid 93 N, 35 ml). The solids were then isolated by filtration, washed with water and dried at 40° C./50 mbar. Yield 22.3 g (=58%), 87.1% w/w.

Example 5

N,N-Dimethyl 2-(N—(N-(4,6-dimethoxypyrimid-2-yl)-aminocarbonyl)-aminosulfonyl)-4-formamido-benzamide (XIV)

A) A mixture of 75 g N,N-Dimethyl 2-(N-(-(4,6-dimethoxy-pyrimid-2-yl)-aminocarbonyl)-aminosulfonyl)-4-nitrobenzamide (XII), sodium molybdate (0.05 g) and Pd/C (3 g, 5%, 50% water) in formic acid (225 ml) was hydrogenated for 3 hours at 30-35° C. The catalyst was filtered and washed with formic acid (20 ml). The filtrate was concentrated in vacuo (35° C.) and ethyl acetate (240 ml) added. After stirring for 1 hour at 45° C. the mixture was cooled to 0-5° C., stirred for a further 2 hours and filtered. After washing with ethyl acetate (2×25 ml) the product was re-suspended in ethyl acetate (200 ml), heated for 2 hours at 50-55° C., cooled to 20° C., filtered, washed with ethyl acetate (2×25 ml) and dried at 45° C./50 mbar. Yield 60.6 g (=83.6%), 95.5% w/w.
B) A mixture of 30 g N,N-dimethyl 2-aminosulfonyl-4-formamidobenzamide (VI*) and 3.3 g (N-(4,6-dimethoxypyrimidin-2yl)phenylcarbamate (3.3 g) in acetonitrile (250 ml) was treated with potassium carbonate (30 g) at 20° C. A further portion of (N-(4,6-dimethoxypyrimidin-2yl)phenylcarbamate (2 g) was added after 3 hours. After a further hour xylene (400 ml) was added and the acetonitrile removed by distillation in vacuo (45° C.). Thereafter hydrochloric acid (1 N, 400 ml) was added, the product filtered, washed with water (2×200 ml), xylene (2×200 ml) and dried. Yield 42 g (=66.1%), 78.7% w/w.

The invention claimed is:
1. A process for the preparation of a compound of the formula (I)

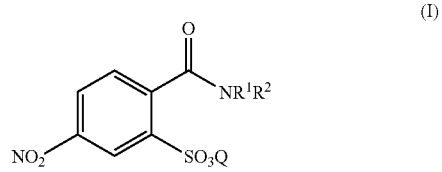

wherein
R$^1$ is methyl,
R$^2$ is methyl, and
Q is a cation;
wherein a compound of formula (III)

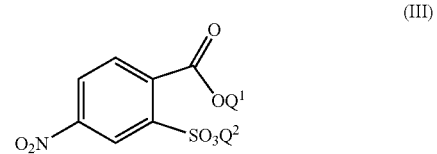

where Q$^1$ and Q$^2$ are identical or different and is a cation is cyclized to form an anhydride of the formula (II)

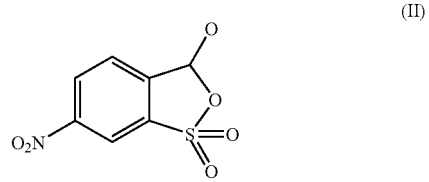

and the compound of formula (II) is reacted with an amine of the formula NHR$^1$R$^2$ or a salt thereof.
2. A process for the preparation of a compound of the formula (I),

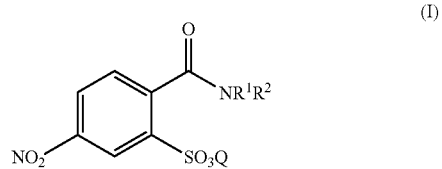

comprising reacting an amine of the formula NHR$^1$R$^2$ or a salt thereof,
wherein
R$^1$ is methyl,
R$^2$ is methyl, and
Q is a cation;

with a diacid salt of the formula (III)

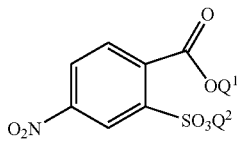
(III)

where $Q^1$ and $Q^2$ are identical or different and is a cation with an activation reagent in a solvent whereby activation reagent is a reagent capable of converting an acid into the acid-chloride or acid anhydride or similarly reactive derivatives of the acid, and amongst other includes phosgene, thionyl chloride, phosphorus oxychloride, phosphorus trichloride, sulfonyl chloride or mixtures thereof.

3. The process according to claim 2, wherein $Q^1$ and $Q^2$ is a sodium cation.

4. The process according to claim 2, wherein $Q^1$ and $Q^2$ is a potassium cation.

5. The process of claim 2, wherein the activation reagent is thionyl chloride.

6. A process for the preparation of a compound of the formula (I)

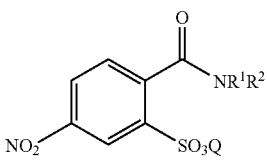
(I)

wherein
$R^1$ is methyl,
$R^2$ is methyl, and
Q is a cation;
which consists of reacting an amine of the formula $NHR^1R^2$ or a salt thereof with a diacid salt of the formula (III)

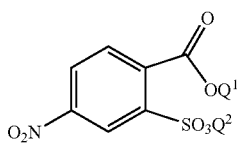
(III)

where $Q^1$ and $Q^2$ are identical or different and is a cation with an activation reagent.

7. The process of claim 6, wherein the activation reagent is thionyl chloride.

8. A process for the preparation of a compound of the formula (I)

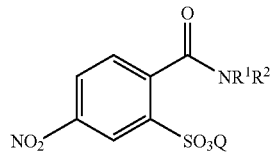
(I)

wherein
$R^1$ is methyl,
$R^2$ is methyl, and
Q is a cation;
wherein a compound of formula (III)

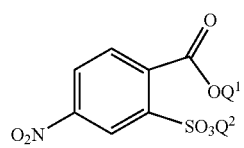
(III)

is cyclized to form an anhydride of the formula (II)

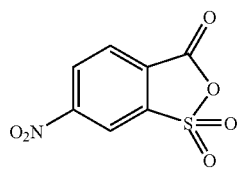

and the compound of formula (II) is reacted with an amine of the formula $NHR^1R^2$ or a salt thereof.

9. A process for the preparation of a compound of the formula (I),

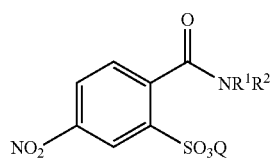
(I)

comprising reacting an amine of the formula $NHR^1R^2$,
wherein
$R^1$ is methyl,
$R^2$ is methyl, and
Q is a cation;
with a diacid salt of the formula (III)

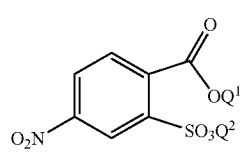
(III)

where $Q^1$ and $Q^2$ are identical or different and is a cation with an activation reagent in a solvent whereby activation reagent is a reagent capable of converting an acid into the acid-chloride or acid anhydride or similarly reactive derivatives of the acid, and amongst other includes phosgene, thionyl chloride, phosphorus oxychloride, phosphorus trichloride, sulfonyl chloride or mixtures thereof.

10. The process according to claim 9, wherein $Q^1$ and $Q^2$ is a sodium cation.

11. The process according to claim 9, wherein $Q^1$ and $Q^2$ is a potassium cation.

12. The process of claim 9, wherein the activation reagent is thionyl chloride.

13. A process for the preparation of a compound of the formula (I),

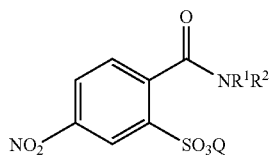

(I)

comprising reacting an amine of the formula $NHR^1R^2$, wherein $R^1$ is methyl, $R^2$ is methyl, and Q is a cation;

with a diacid salt of the formula (III)

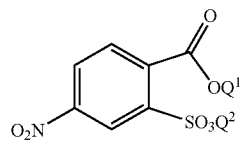

(III)

where $Q^1$ and $Q^2$ are identical or different and is a cation with an activation reagent.

14. The process of claim 13, wherein the activation reagent is thionyl chloride.

* * * * *